United States Patent [19]

Farquharson et al.

[11] Patent Number: 5,062,713

[45] Date of Patent: Nov. 5, 1991

[54] METHOD FOR DETERMINING THE RESIDENCE TIME DISTRIBUTION OF A POLYMER EXTRUDER

[75] Inventors: Stuart Farquharson, Freeport; Peter T. Keillor, III, West Columbia, both of Tex.

[73] Assignee: The Dow Company, Midland, Mich.

[21] Appl. No.: 608,066

[22] Filed: Nov. 1, 1990

Related U.S. Application Data

[63] Continuation of Ser. No. 403,552, Sep. 6, 1989, abandoned.

[51] Int. Cl.$^5$ .................. G01I 3/46; G01N 21/25; G01J 3/42
[52] U.S. Cl. .................. 356/402; 356/416; 356/419; 356/414
[58] Field of Search .................. 356/402–411, 356/416, 419, 320, 414

[56] References Cited

U.S. PATENT DOCUMENTS

| | | | |
|---|---|---|---|
| 4,193,694 | 3/1980 | Smith .................. | 356/411 |
| 4,367,041 | 1/1983 | Webb, Jr. et al. .................. | 356/411 |
| 4,464,054 | 8/1984 | Karras et al. .................. | 356/406 |

FOREIGN PATENT DOCUMENTS 2162308  1/1986  United Kingdom .

OTHER PUBLICATIONS

Farquharson et al; "Extruder Mixing Analysis via a Fiber Optically Coupled Visible Spectraphotometer", Chemical, Biochemical and Environmental Applications of Fibers, 990, 1988.
Delahay, Instrumental Analysis, 5th Printing, pp. 215–216, 1967.
Skoog et al; Fundamentals of Analytical Chemistry, pp. 663–664, 1963.
David B. Todd, Residence Time Distribution in Twin-Screw Extruders, Polymer Engineering and Science, 15(6), 437–443 (1975).

Primary Examiner—F. L. Evans
Assistant Examiner—K. P. Hantis
Attorney, Agent, or Firm—Timothy S. Stevens

[57] ABSTRACT

A method for the on-line determination of the residence time distribution of a polymer extruder by injecting a quantity of dye, such as Mobay Red 5B, into the feed throat of the extruder and then photometrically monitoring the polymer flowing from the extruder for the dye. The advance of the present invention is to direct a single beam of polychromatic light through the polymer flowing from the extruder, e.g., by using a quartz-halogen light source and an optical fiber, and then to split this single beam of light that has passed through the polymer into two beams, e.g., by the use of a bifurcated optical fiber, each of which resulting beams are then passed through a separate filter to a separate photodetector. The wavelength of maximum transmission of one of the filters is selected to be near the wavelength of maximum light absorption of the dye so that the signal from the photodetector associated with this filter is a function of the concentration of the dye in the polymer flowing from the extruder. The wavelength of maximum transmission of the other filter is selected to be near the wavelength of minimum light adsorption of the dye and the polymer so that the signal from the photodetector associated with this filter is a function of the background light absorption of the polymer flowing from the extruder. The noise level of the dye concentration signal can be a problem due to bubbles and inclusions in the polymer flowing from the extruder and this noise level is substantially reduced by correcting the dye concentration signal with the background signal.

1 Claim, 2 Drawing Sheets

METHOD FOR DETERMINING THE RESIDENCE TIME DISTRIBUTION OF A POLYMER EXTRUDER

BACKGROUND OF THE INVENTION

This is a continuation of application Ser. No. 403,552, filed Sept. 6, 1989, now abandoned.

Extruders play a vital role in blending and compounding in the polymer industry. In addition, more recently polymerization has been carried out in extruders. The design of the extruder is not only application dependent but is also critical for optimum performance. Unfortunately, the selection of extruder elements is based on experience rather than rigorous engineering principals with system optimization occurring through a series of trial and error adjustments. A standard method for assisting this optimization process is measuring the residence time distribution (RTD) of a quantity of titanium dioxide after it has passed through the extruder. The RTD is obtained by adding a given amount titantium dioxide to the feed throat of the extruder and then sampling the polymer emerging from the extruder every five seconds for a number of minutes. A lab analysis is then made on the collected samples to determine the concentration of titanium dioxide in each of the collected samples v. time to determine the RTD of the extruder. One probelm with this method is the relatively long time needed to analyze all of the collected samples in a laboratory. Another problem with this method is the relativley high cost of each RTD determination. A new method for determining the RTD of a polymer extruder that reduced these problems would be an advance in this art.

SUMMARY OF THE INVENTION

The present invention is a method for the on line determination of the RTD of a polymer extruder which reduces the above mentioned problems. The present invention includes seven steps. The first step is to flow a polymer from the polymer extruder. The second step is to introduce a tracer chemical into the extruder. The tracer chemical must have a first wavelength of absorption of light where its absorbency of light is greater than its absorbency of light at a second wavelength. The third step is to pass a beam of polychromatic light, such as light from an incandescent lamp, through the polymer flowing fron the polymer extruder. The fourth step is to split the beam of light that passed through the polymer flowing from the polymer extruder into a first part and a second part, such as by the use of a bifurcated optical fiber or a beam splitter. The fifth step is to direct the first part of the split beam through a first optical filter to a first photodetector to generate a first signal. The wavelength of maximum transmission of the first filter is near the first wavelength of absorption of the tracer chemical. The first signal is thus a function of the concentration of the tracer chemical in the polymer but can be seriously interfered with, i.e., made noisy, by bubbles or inclusions in the polymer flowing from the extruder. The sixth step is to direct the second part of the split beam through a second optical filter. The wavelength of maximum transmission of the second filter is near the second wavelength of the absorption of the tracer chemical. The second signal is more of a function of the background absorbency of the polymer flowing from the extruder than the first signal. The last step is to correct the first signal with the second signal, i.e. to reduce the noise of the first signal, to obtain a signal over time after the second step that represents the residence time distribution of the polymer extruder.

DETAILED DESCRIPTION OF THE INVENTION

Figure 1:
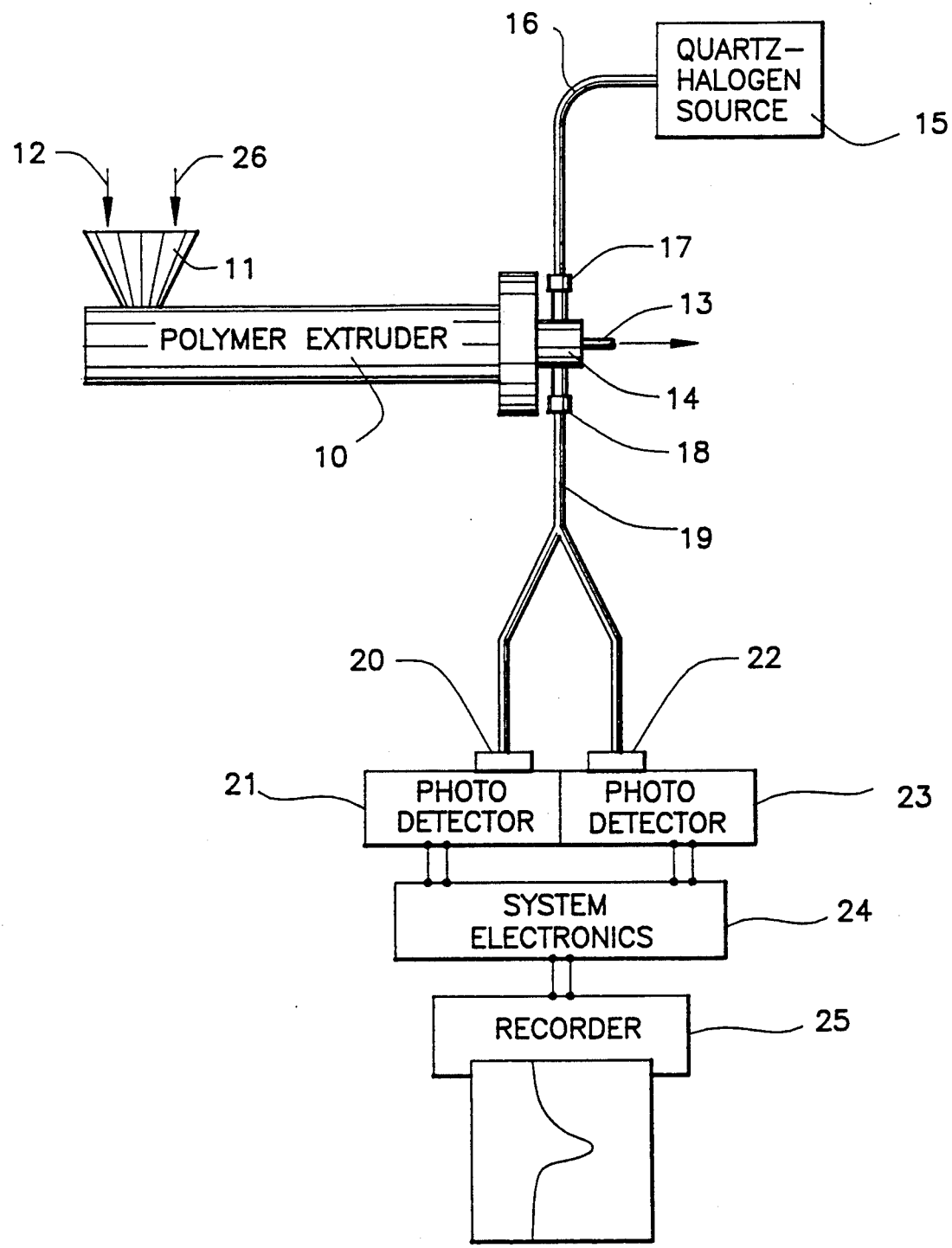
FIG. 1 shows a side view of a polymer extruder being studied to determine its residence time distribution according to the present invention and includes apparatus suitable for for this determination, shown mostly in schematic form, including a pair of fiber optic probes inserted into the outlet die of the extruder.
Figure 2:
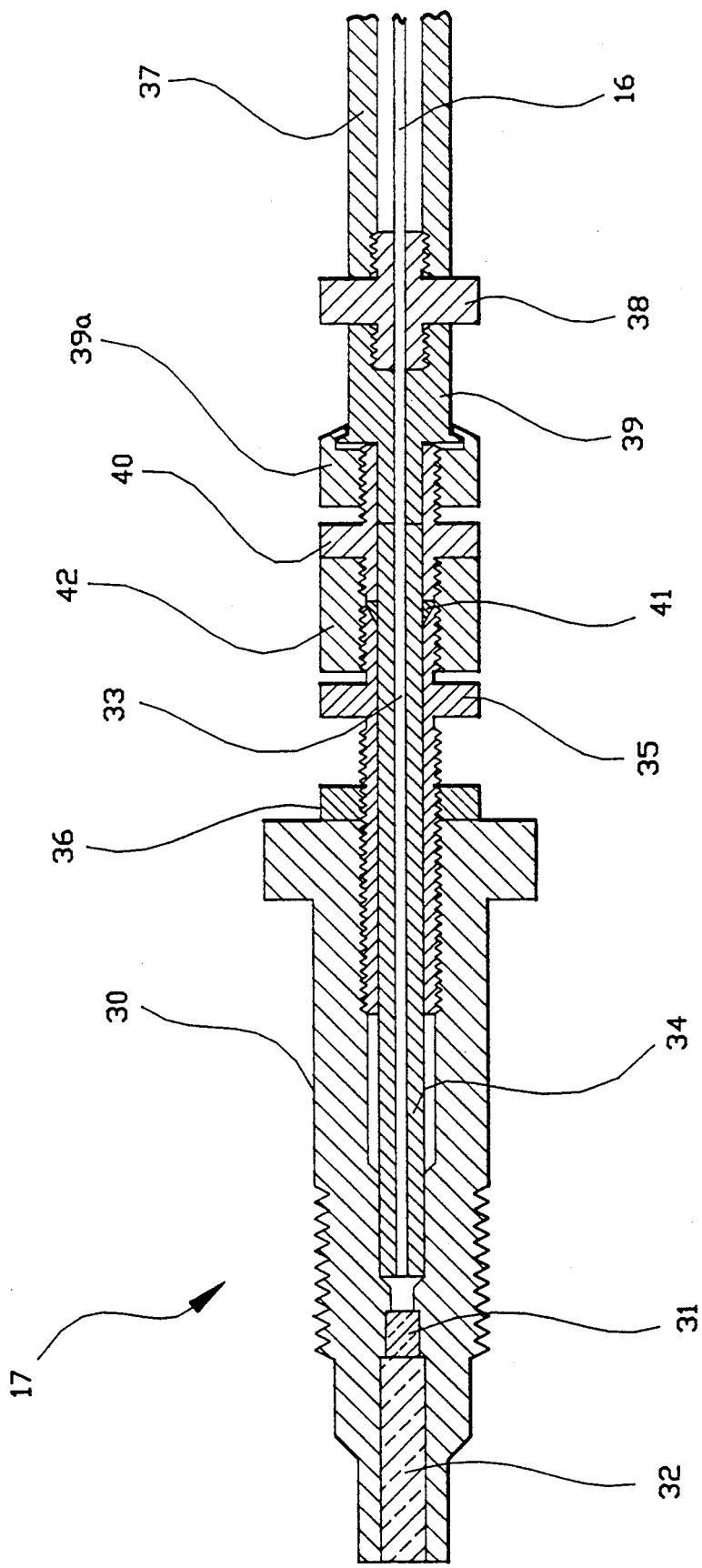
FIG. 2 is a cross-sectional drawing of one of the fiber optic probes shown in FIG. 1.

Referring now to FIG. 1, therein is shown a polymer extruder 10 having a feed throat 11. Polymer pellets 12 are continuously poured into the feed throat 11 and are melted and mixed in the extruder 10. The melted and mixed polymer then flows from the extruder 10 as a stream of molten polymer 13 via an output die 14. A source of polychromatic light is shown as the quartz-halogen light source 15. An optical fiber 16 is used to direct light from the source 15 to a fiber optic probe 17. FIG. 2 shows a cross sectional view of the fiber optic probe 17 which will be discussed in more detail below. The light from the probe 17 passes through the stream of melted polymer 13 and enters a fiber optic probe 18. A bifurcated optical fiber is used to direct a first part of this light through a first optical filter 20 to a first photodetector 21 and a second part of this light through a second optical filter 22 to a second photodetector 23. The first photodetector 21 is used to generate an electrical signal which is sent to the system electronics 24. The second photodetector 23 is used to generate a second electrical signal which is also sent to the system electronics 24 which processes both of these signals to produce a corrected signal which is sent to the strip chart recorder 25.

An injection of tracer chemical or dye 26 is made into the feed throat 11. The dye 26 must have a first wavelength of absorption of light where its absorbency of light is greater than its absorbency of light at a second wavelength. The dye moves through the extruder 10 and emerges in the stream of molten polymer 13 according to the residence time distribution of the extruder 10, i.e., the dye is dispersed in the melted polymer in the extruder 10 and emerges in the stream 13 according to a dye concentration v. time relationship that is indicative of the residence time distribution of the extruder 10. The beam of light passed through the stream of polymer 13 from the probe 17 to the probe 18, is split by the bifurcated optical fiber 19 and detected by the photodetectors 21 and 23 after passing through the optical filters 20 and 22 respectively. The wavelength of maximum transmission of the first filter 20 must be near the first wavelength of absorption of the injected dye 26 so that the first signal is a function of the concentration of dye in the polymer stream 13.

Theoretically, it should be possible to determine the residence time distribution from the first signal only. However, it often happens that the first signal is too noisy for practical use. The first signal, to be useful, must be corrected for this noise, the source of which is not completely understood but which is believed to be often caused by bubbles and other inclusions in the polymer stream 13.

This noise problem is reduced in the present invention by generating a second signal which is used to substantially correct the first signal. To do this the wavelength of maximum transmission of the second filter 22 must be near the second wavelength of absorption of the dye so that the signal from the second photodetector 23 is more of a function of the background absorbance of the polymer stream 13 than the first signal, the more so the better of course. The system electronics 24 processes the first and second signals to obtain a corrected signal that is substantially less noisy.

Because the stream 13 is moving rapidly, it does not work well to pass two beams of light through different regions of the polymer stream 13, each beam having a different wavelength, to obtain the same result as the present invention. It also does not work well to wavelength scan a single beam of light through the polymer stream 13 using scan times on the order of ten seconds. It is critical in the present invention to pass a single polychromatic beam of light through substantially a single space region of the polymer stream 13 and then split this beam of light so that a two wavelength analysis of substantially the same space region of the polymer stream 13 can be made substantially simultaneously.

A polychromatic beam of light is a beam of light made up of at least the first and second wavelengths of maximum light transmission of the first and second filters. The preferred source for polychromatic light is a quartz-halogen lamp. The preferred means for directing the beams of light is by the use of fiber optics. The preferred means for splitting the beam of light after it has passed through the polymer stream is by the use of a bifurcated optical fiber or a bifurcated fiber optic bundle. However, a bifurcated optical fiber or bundle is not essential and good results can be had by simply having two optical fibers be adjacent, co-directional and co-terminus at one end and separated at the other end or a bundle of such fibers. Alternatively, lenses, mirrors and beam splitters can be used to direct the light beam and split it.

The dye 26 must have a first wavelength of absorption of light where its absorbency of light is greater than its absorbency of light at a second wavelength. The specific tracer chemical or dye used is not critical in the present invention as long as it meets the above criteria. If the polymer itself is colored, then it is better to select the dye so that the first and second wavelengths of absorption of the dye are not near the maximum absorption of light of the polymer.

A simple system electronics 24 can be had by electrically subtracting the second signal from the first signal and then plotting the resulting signal on the recorder 25. This plot will approximately represent the residence time distribution of the extruder.

A more sophisticated, accurate and preferred approach is to correct the first signal with the second signal using a computer as follows. An analog to digital converter is used to alternatively and sequentially convert the magnitude of the first and second signals to digital form at a given rate such as 1800 times per second and store this data in a buffer in a random access memory block of the computer. Then, periodically, such as once per second, these digitized signals are averaged and stored as a function of time as a data set for each signal for the period of time. If the polymer flowing from the extruder contains bubbles, inclusions or for another reason the signals are noisy, then a least squares linear fit of the data sets is made to obtain the slope and intercept of the data line. If the application is one where no substantial noise is present then the slope is taken as the average stored first signal magnitude divided by the average stored second signal magnitude and the intercept is taken as zero. Then the tracer chemical is introduced into the extruder and data collected for each time period according to the following formula:

$$C = -\log [FS \div ((S \times SS) + I)]$$

where: C is the relative concentration of the tracer chemical in the stream of polymer flowing from the extruder; FS is the magnitude of the first signal; S is the slope as discussed above; SS is the magnitude of the second signal; and I is the intercept as discussed above.

The C v. time data represents the retention time distribution of the extruder which can be displayed on a video screen and printed out in various forms as is well known in the art. The data can be post run processed to quantitate such things as the mean and median residence time and the skew of the residence time distribution.

In the discussion above, two ways were presented for correcting the first signal with the second signal to reduce the noise of the first signal. It should be understood that many other ways for doing this are possible and are within the scope of the invention as long as the first signal is operated on some way with the second signal to reduce noise, i.e., to obtain a corrected signal, that over time after introducing the tracer chemical into the extruder represents the residence time distribution of the extruder. It should also be understood that the term signal as used in the present invention includes an analog signal as well as a digital derivative of an analog signal.

Referring now to FIG. 2, therein is shown a detailed cross-sectional drawing of the probe 17 shown in FIG. 1. The probe 17 has a body 30 which is a blank stainless steel Dynisco brand thermal probe which has been bored through its long axis to accept various elements as will be discussed below. A Nippon Electric Corporation 3 millimeter diameter SELFOC GRIN lens 31 is positioned in a 3 millimeter diameter section of the bore of the body 30. A 0.125 inch diameter sapphire rod 32 is sealed in a 0.125 inch diameter section of the body 30 by placing an annular bead of Sauerreisen Electrotemp ceramic cement #8 and then an annular bead of Huntington VS 101 epoxy cement on the rod 32 and then inserting the rod 32 into the body 30. The combination of the ceramic and the epoxy cement provides a seal that resists both chemical and thermal degradation. A four inch long section of Ensign Bickford HCP 600 micrometer optical fiber 33 is coated with epoxy resin and then inserted into a four inch long section of Valco 0.125 inch outside diameter, 0.039 inch inside diameter, Micropore precision capillary tubing 34. A Swagelock SS-200-61 bulkhead union 35 is bored through its long axis with a 0.125 inch drill to pass the tubing 34 and the union 35 is screwed into the body 30 and locked to it by a lock nut 36. The optical fiber 16 is another section of Ensign Bickford HCP 600 micrometer optical fiber encased and protected by 0.25 inch diameter Greenfill flexible hose 37. The optical fiber 16 passes through a Swagelock SS-200-61 reducing union 38 and is epoxied into and terminates at the end of an OFTI SMA-5600 fiber optic connector 39 which has been tapped with 10-32 threads to thread onto the union 38. The connector 39 is screwed via the slip nut 39a of the connector 39 onto a OFTI SMA-2220 fiber optic coupler 40 which has been bored through its long axis with a 0.125 inch diameter drill. A 0.125 inch Swagelock tubing nut 42 is drilled and tapped with 0.25 inch-36 threads to screw onto the coupler 40. The end of the coupler 40 presses against a 0.125 inch Swagelock ferrule 41 which in turn locks the tubing 34 in the union 35.

The probe 17 is adjusted for use by shining light into the fiber 16 and projecting this light onto a flat object approximately an inch from the end of the rod 32. The lock nut 36 is loosened and the union 35 is screwed into and out of the body 30 to find the position where the beam of light coming from the probe 17 is collimated. Then the locknut 36 is tightnened to lock in this adjustment.

One of the benefits of the probe 17 is that once it is so adjusted, it can be replaced without disturbing this adjustment by breaking the connection between the connector 39 and the coupler 40 via the nut 39a. Another benefit of the probe 17 is the GRIN lens 31 is easier to align than a conventional lens. The use of the precision capillary tubing 34 insures that the optical fiber 33 will be substantially centered in the field of view of the lens 31.

The probe 18 as shown in FIG. 1 is identical to the probe 17 shown in FIG. 2 but the optical fiber 19 is a bifurcated optical fiber, such as a C-Technology bifurcated optical fiber. Alternatively, a pair of optical fibers can be routed through the connector 39, the union 38 and the flexible hose 37 to be co-terminus at the end of the connector 39 but separated at their other ends to direct light through the first filter 20 and the second filter 22.

The die 14 is bored and tapped for the probe 17 and the probe 18 so that the probes are in line and across from one another so that the beam of light generated by the source 15 and directed by the optical fiber 16 is shown through the polymer stream 13 just before it emerges from the extruder 10.

Generally, the tracer chemical 26 is introduced at the feed throat 11 of the extruder 10. However, it should be understood that the tracer chemical 26 can be introduced into the exterior 10 at other places such as at a vent, through a thermal port, into a mixing block and so forth. Repeated determination of the RTD of the extruder 10 by introducing the tracer chemical 26 at various points along the extruder can indicate the influence of the various sections of the extruder on its overall RTD.

EXAMPLE

The system shown in FIGS. 1 and 2 and partly specified above is assembled using a Werner & Pfleiderer ZSK-30 twin screw extruder to extrude a polymer under conditions where the extruder is not run liquid full. The tracer chemical is Mobay Red 5B dye which absorbs substantially more visible light at 530 nanometers than at 640 nanometers. The first filter 20 is a Corion #P10-530-A filter having a maximum transmission at about 530 nanometers. The second filter 22 is a Corion #P10-640-A filter having a maximum transmission at about 640 nanometers. The first photodetectors 21 and the second photodetectors 23 are a United Detector Technology #PIN-5DP units. The 100-300 millivolt output of each detector is amplified by Action Instruments Model AP-4310 transmitters, modified to provide a 30-50 megohms impedance, and fed to a Metrabyte Corporation Model Dash-8 A/D board in an IBM PC-AT digital computer. A/D conversions are performed alternatively and sequentially at a rate of 1800 per second and written to a 60-word buffer in RAM. Each buffer is sampled once per second, the data sorted into the two channels and averaged. This procedure insures that the data for the two channels is substantially simultaneous which is necessary due to the short time required for a bubble to move through the light path. The data is treated in the computer as described above according to a simple BASIC program, saved in a BASIC array according to elapsed time and displayed on the video screen of the computer.

After the slop and intercept are determined as described above, a solenoid actuated automatic injection valve is used to inject the dye into the extruder at the feed throat and to initiate the collection of data to determine the residence time distribution of the extruder under various operating conditions such as the rotation rate of the screws and the temperature of the various sections of the extruder. The relative concentration of the dye in the polymer stream flowing the extruder v. time plot of the data shows no apparent dye seen until about 175 seconds. Then the relative concentration of the dye rises to a maximum at about 200 seconds, then falls to ten percent of the maximum value at about 300 seconds and to less than one percent of the maximum value at about 500 seconds. Repeated determinations of the residence time distribution of the extruder are made under different extruder operating conditions to aid in the optimization of the operation of the extruder.

What is claimed is:

1. A method for determining the residence time distribution of a polymer extruder on the line, comprising the steps of:

(a) flowing a polymer from the polymer extruder;

(b) introducing a tracer chemical into the extruder, the tracer chemical having a first wavelength of absorption of light where its absorbency of light is greater than its absorbency of light at a second wavelength;

(d) passing a beam of polychromatic light through the polymer flowing from the polymer extruder;

(e) splitting the beam of the light passed through the polymer flowing from the polymer extruder into a first part and a second part;

(f) directing the first part through a first optical filter to a first photodetector to generate a first signal, the wavelength of maximum transmission of the first filter being near the first wavelength of absorption of the tracer chemical, the first signal being a function of the concentration of the tracer chemical in the polymer;

(g) directing the second part through a second optical filter and to a second photodetector to generate a second signal, the wavelength of maximum transmission of the second filter being near the second wavelength of absorption of the tracer chemical, the second signal being a function of the background absorbency of the polymer;

(h) correcting the first signal with the second signal to obtain a signal that over time after step (b) represents the residence time distribution of the polymer extruder.

* * * * *